(12) United States Patent
Huang et al.

(10) Patent No.: US 9,157,844 B2
(45) Date of Patent: Oct. 13, 2015

(54) BENDING TESTING

(71) Applicant: DMAR ENGINEERING, INC., Houston, TX (US)

(72) Inventors: Zhiming Huang, Missouri City, TX (US); Dagang Zhang, Houston, TX (US)

(73) Assignee: DMAR Engineering, Inc., Houston, TX (US)

( * ) Notice: Subject to any disclaimer, the term of this patent is extended or adjusted under 35 U.S.C. 154(b) by 39 days.

(21) Appl. No.: 14/288,366

(22) Filed: May 27, 2014

(65) Prior Publication Data

US 2015/0233805 A1    Aug. 20, 2015

Related U.S. Application Data

(60) Provisional application No. 61/940,840, filed on Feb. 18, 2014.

(51) Int. Cl.
*G01N 3/20* (2006.01)
*E21B 49/00* (2006.01)

(52) U.S. Cl.
CPC .............. *G01N 3/20* (2013.01); *E21B 49/001* (2013.01); *E21B 49/003* (2013.01)

(58) Field of Classification Search
CPC .................................. G01N 3/20; G01L 1/04
USPC ............................. 73/852, 862.622, 862.621
See application file for complete search history.

(56) References Cited

U.S. PATENT DOCUMENTS

| | | | | |
|---|---|---|---|---|
| 4,666,006 A | * | 5/1987 | Wernimont | G01G 21/13 177/211 |
| 5,029,483 A | * | 7/1991 | Gautschi | G01G 19/44 73/172 |
| 2011/0036183 A1 | * | 2/2011 | Artale | A61B 19/46 73/862.621 |

* cited by examiner

*Primary Examiner* — Jewel V Thompson
(74) *Attorney, Agent, or Firm* — Liaoteng Wang

(57) ABSTRACT

Apparatus and methods related to bending testing are described. For example, some embodiments may contain a clamp with pivot pin, pellet, tensioning device, and supporting platform, which can be used for testing the bending characteristics, such as bending stiffness, of a testing sample, which can be slender structures such as umbilicals, flexibles, and rigid pipes.

9 Claims, 3 Drawing Sheets

BENDING TESTING

CROSS REFERENCE TO RELATED APPLICATIONS

This application claims the benefit of U.S. Provisional App. No. 61/940,840, filed on Feb. 18, 2014, which is incorporated herein by reference.

FIELD OF PRESENT DISCLOSURE

This present disclosure relates to bending testing.

BACKGROUND INFORMATION

During oil and gas underwater field development, some more and more commonly used subsea equipment include slender structures such as umbilicals, flexibles, and rigid pipes. These slender structures have strong non-linear bending characteristics. Thus, linearized approximations of the bending stiffness of these slender structures are oftentimes not sufficient for ascertaining the bending characteristics of such structures. At the same time, the more complex non-linear bending characteristics cannot be derived directly from theoretical calculations alone. Apparatus and methods have been proposed for conducting bending testing to obtain the accurate bending characteristics of these slender structures.

DETAILED DESCRIPTION

Figure 1:
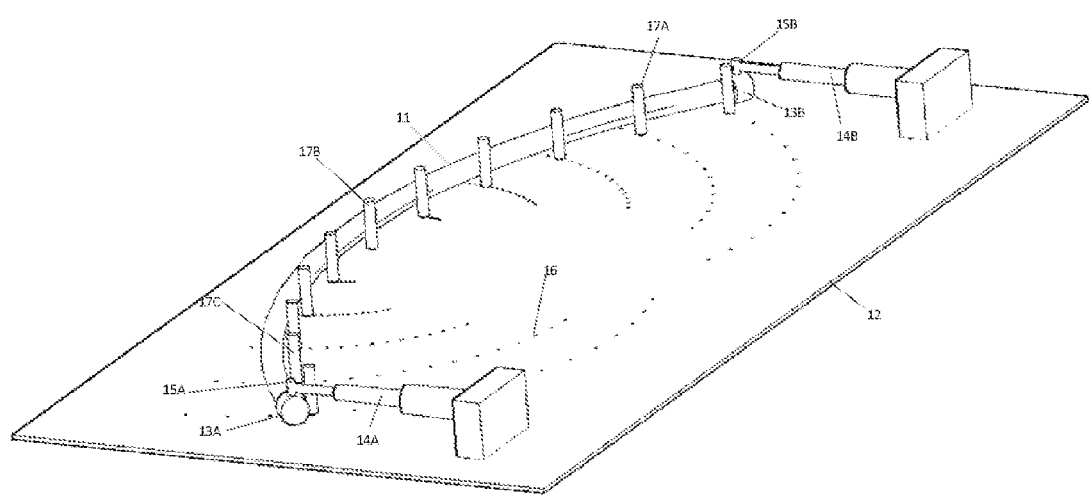
FIG. 1 is a diagram showing the overview of an embodiment of the bending testing apparatus.

This document discloses apparatus and methods related to bending testing. FIG. 1 shows an implementation of the apparatus and methods for bending testing. The bending testing for a testing sample 11 can be performed on a testing platform 12. The testing sample 11 is fastened by two fasteners 13A and 13B on each end. The fasteners 13A and 13B are further attached to two extendable and retractable arms 14A and 14B that can be attached to the testing platform 12. The fasteners 13A and 13B can be clamps, which can be further attached to the extendable and retractable arms 14A and 14B through two pivot pins 15A and 15B (or chain links, shackles, or other devices). The extendable and retractable arms 14A and 14B can be two hydraulic cylinders, winches, or other tensioning devices. The testing sample 11 can be positioned on the testing platform 12 along one or more pellets 17A, 17B, and 17C. The pellets 17A, 17B and 17C can be attached to the testing platform 12 by fitting into the pre-drilled holes 16 on the testing platform 12. The pre-drilled holes 16 can be arranged in a defined pattern. For example, the pattern can be defined according to the formula $X=R*\sin[L/R]$, and $Y=R*(\cos[L/R]-1)$, wherein R is the bending radius, L is the sample half length, and X and Y are the coordinates for the pre-drilled holes 16 on the testing platform 12. The pellets 17A, 17B and 17C can be placed into the pre-drilled holes according to a defined pattern to help maintain a certain shape or curvature of the testing sample 11.

Figure 2:
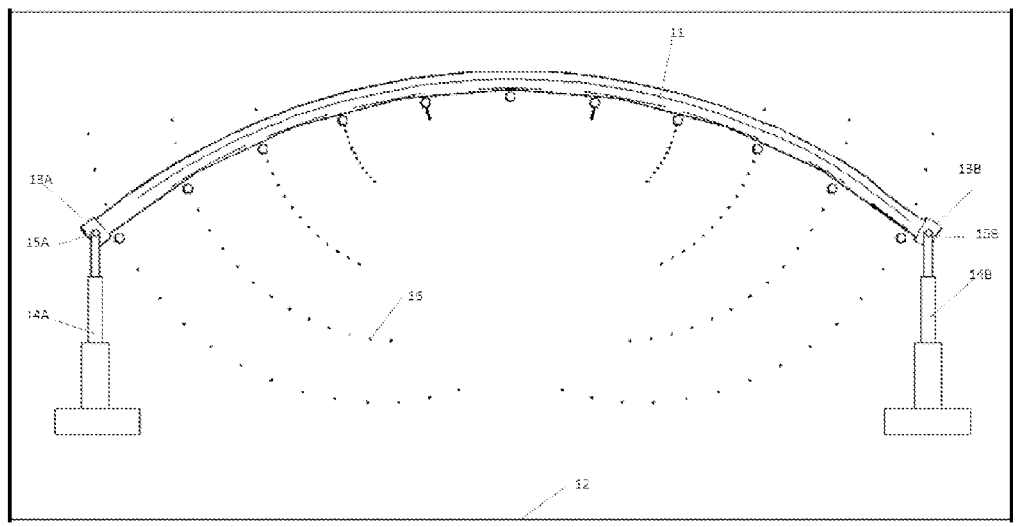
FIG. 2 is a diagram showing the top view of an embodiment of the bending testing apparatus.

FIG. 2 shows the top view of an implementation of the apparatus and methods for bending testing. A plurality of pellets is used to help maintain a uniform curvature and constant bending radius.

Figure 3:
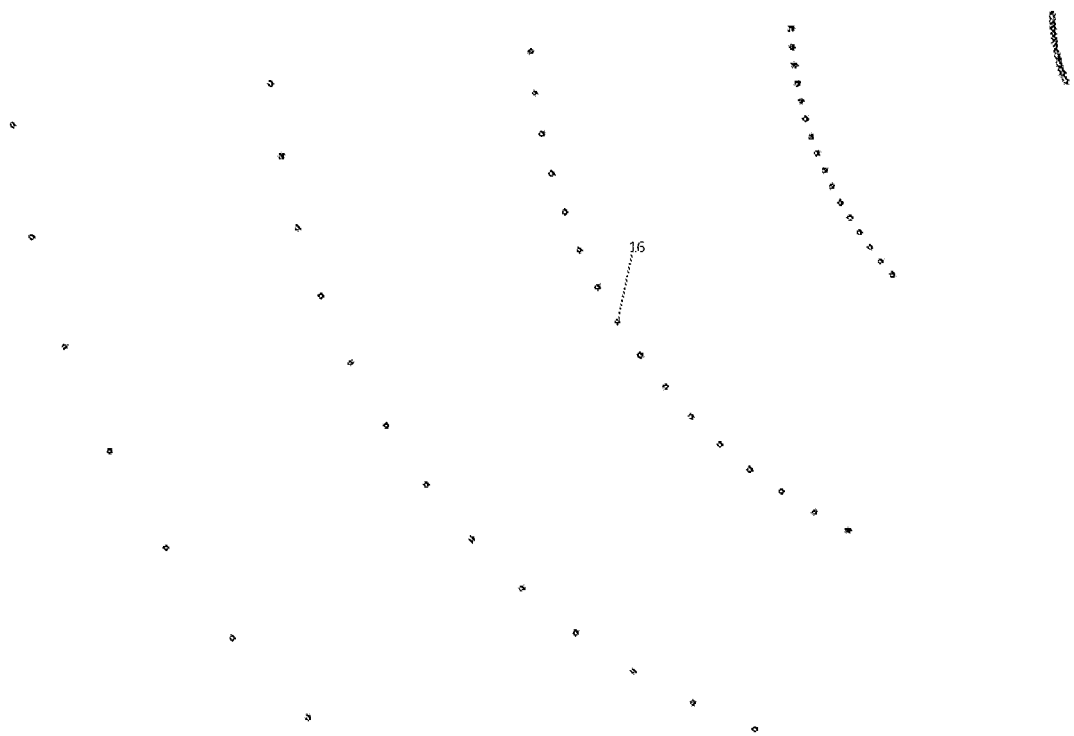
FIG. 3 is a diagram showing the zoomed-in view of the pattern of the holes pre-drilled on the testing platform of an embodiment of the bending testing apparatus.

FIG. 3 shows the zoomed-in view of the pattern of the holes pre-drilled on the testing platform of an implementation of the apparatus and methods for bending testing. The pellets can tightly fit in the pre-drilled holes on the testing platform, and can be moved from one hole to another based on the desired shape and curvature. The pellets can have threads at one end. The pellets can also be attached to the testing platform through a separate nut. The pellets can also have lock pin holes, and can be attached to the testing platform through a locking pin.

In some implementations, the testing sample can be about five meters in length. Two clamps can be used to hold the two ends of the testing sample, and prevent slippage between adjacent parts of the testing sample, such as umbilical tubes or flexible layers. The clamps can have pivot pins to allow them to rotate freely, and the pivot pins can be controlled by a tensioning device, such as hydraulic cylinders. The hydraulic cylinders can pull the testing sample to wrap around the pellets, and the hydraulic cylinder pulling loads can be recorded.

In some implementations, the bending testing can be conducted as follows: (i) lay the testing sample on the testing platform; (ii) fasten the ends of the testing sample; (iii) position the pellets to the arc with desired radius; (iv) activate the hydraulic cylinders to pull the testing sample against the pellets; and (v) record the hydraulic cylinder tension time histories. From the tension time histories, the minimum tension required to achieve the desired bending radius can be derived. This minimum tension can then be decomposed into testing sample axial direction and normal direction, based on which the bending moment can be calculated. This bending moment can be the output of the testing result. When the steps above are completed, the hydraulic cylinders can be slacked slightly, and the pellets can be moved to the next testing radius, so that additional tests can be repeated at different radiuses.

OTHER EMBODIMENTS

Various other adaptations and combinations of features of the embodiments and implementations disclosed are within the scope of the present disclosure. It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An apparatus for bending testing, comprising:
    a testing platform;
    a fastener for fastening the end of a testing sample;
    a pellet mounted on the testing platform for further positioning the testing sample on the testing platform; and
    an extendable and retractable arm connected to the fastener.

2. An apparatus according to claim 1, wherein the testing platform comprises pre-drilled holes arranged in a defined pattern.

3. An apparatus according to claim 2, wherein the defined pattern is given by the following formula:

$$X=R*\sin[L/R]; Y=R*(\cos[L/R]-1)$$

Wherein R is the bending radius, L is the sample half length, and X and Y are the coordinates for the pre-drilled holes.

4. An apparatus according to claim 2, wherein the pellet is mounted on the testing platform through a pre-drilled hole.

5. An apparatus according to claim 1, wherein the fastener comprises a clamp that can rotate freely around a pivot pin, a chain link, or a shackle.

6. An apparatus according to claim 1, wherein the extendable and retractable arm is a hydraulic cylinder.

7. An apparatus according to claim 6, wherein the hydraulic cylinder is attached to the testing platform.

8. An apparatus according to claim 1, wherein the pellet has a curved surface for supporting the testing sample.

9. A method for bending testing, comprising:
placing a testing sample on a testing platform;
fastening the end of the testing sample;
positioning one or more pellets along an arc with desired radius;
pulling the testing sample against the pellets through an extendable and retractable arm connected to the fastened end; and
recording the tension time history of the extendable and retractable arm.

* * * * *